United States Patent
Sasaki et al.

(10) Patent No.: US 11,435,286 B2
(45) Date of Patent: Sep. 6, 2022

(54) PATHOGEN DETECTION APPARATUS AND PATHOGEN DETECTION METHOD

(71) Applicant: Panasonic Intellectual Property Management Co., Ltd., Osaka (JP)

(72) Inventors: Yoshiki Sasaki, Osaka (JP); Tatsurou Kawamura, Kyoto (JP); Hiroto Yanagawa, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 304 days.

(21) Appl. No.: 16/908,788

(22) Filed: Jun. 23, 2020

(65) Prior Publication Data
US 2020/0319106 A1 Oct. 8, 2020

Related U.S. Application Data

(63) Continuation of application No. PCT/JP2019/007431, filed on Feb. 27, 2019.

(30) Foreign Application Priority Data
Mar. 28, 2018 (JP) .................. JP2018-063330

(51) Int. Cl.
*G01N 21/64* (2006.01)
*G01N 33/569* (2006.01)
*G01N 33/58* (2006.01)

(52) U.S. Cl.
CPC ....... *G01N 21/64* (2013.01); *G01N 33/56983* (2013.01); *G01N 33/582* (2013.01);
(Continued)

(58) Field of Classification Search
CPC ............ G01N 21/64; G01N 33/56983; G01N 33/582; G01N 2201/06113;
(Continued)

(56) References Cited

U.S. PATENT DOCUMENTS

| 2007/0003997 A1* | 1/2007 | Kemmochi ............. C12Q 1/04 435/34 |
| 2015/0010902 A1 | 1/2015 | Takenaka et al. |
| 2017/0191974 A1 | 7/2017 | Tamura |

FOREIGN PATENT DOCUMENTS

| JP | 11-178814 | 7/1999 |
| JP | 2007-271482 | 10/2007 |

(Continued)

OTHER PUBLICATIONS

International Search Report of PCT application No. PCT/JP2019/007431 dated Jun. 4, 2019.

*Primary Examiner* — Kiho Kim
(74) *Attorney, Agent, or Firm* — Wenderoth, Lind & Ponack, L.L.P.

(57) ABSTRACT

A pathogen detection apparatus includes a collector that collects a pathogen in air; a reactor that causes the pathogen collected by the collector to react with a labeled substance; a time measurer that measures time from start of reaction in the reactor; a detector that detects a quantity of labeled substance that has reacted with the pathogen; and a controller. The controller calculates a gradient value on the basis of a predetermined time period from the start of reaction measured by the time measurer and the quantity of labeled substance detected by the detector, and determines, on the basis of the gradient value, a time interval to next collection that is to be performed by the collector.

8 Claims, 12 Drawing Sheets

(52) U.S. Cl.
CPC .............. *G01N 2201/06113* (2013.01); *G01N 2333/11* (2013.01); *G01N 2458/00* (2013.01)

(58) Field of Classification Search
CPC ........... G01N 2333/11; G01N 2458/00; G01N 1/2211; G01N 21/6408; G01N 2001/2217; G01N 2001/383; G01N 2001/388; G01N 21/648; C12M 1/34
See application file for complete search history.

(56) References Cited

FOREIGN PATENT DOCUMENTS

| | | |
|---|---|---|
| JP | 2012-052866 | 3/2012 |
| JP | 2015-224991 | 12/2015 |
| JP | 2017-009521 | 1/2017 |
| WO | 2013/118259 | 8/2013 |

\* cited by examiner

PATHOGEN DETECTION APPARATUS AND PATHOGEN DETECTION METHOD

BACKGROUND

1. Technical Field

The present disclosure relates to a pathogen detection apparatus and a pathogen detection method that detect the presence or absence of a pathogen by using binding or reaction between the pathogen or a part thereof and a labeled substance.

2. Description of the Related Art

Japanese Unexamined Patent Application Publication No. 2012-52866 discloses a virus collection apparatus that collects viruses in low concentration in the air by using a cyclone and performs analysis to detect a virus in real time.

SUMMARY

In the technique disclosed in Japanese Unexamined Patent Application Publication No. 2012-52866, however, consumables and energy are uniformly consumed to perform detections even when the quantity of virus is small. Thus, consumables or energy is wasted.

One non-limiting and exemplary embodiment provides a pathogen detection apparatus and a pathogen detection method that are capable of reducing detection frequency to reduce waste of consumables or energy.

In one general aspect, the techniques disclosed here feature a pathogen detection apparatus including a collector that collects a pathogen in air; a reactor that causes the pathogen collected by the collector to react with a labeled substance; a time measurer that measures time from start of reaction in the reactor; a detector that detects a quantity of labeled substance that has reacted with the pathogen; and a controller. The controller calculates a gradient value on the basis of a predetermined time period from the start of reaction measured by the time measurer and the quantity of labeled substance detected by the detector, and determines, on the basis of the gradient value, a time interval to next collection that is to be performed by the collector.

It should be noted that general or specific embodiments may be implemented as a method, a system, an integrated circuit, a computer program, a computer-readable recording medium, or any selective combination thereof. The computer-readable recording medium includes, for example, a nonvolatile recording medium, such as a compact disc-read only memory (CD-ROM).

According to one embodiment of the present disclosure, a lower detection frequency enables a reduction in waste of consumables or energy. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
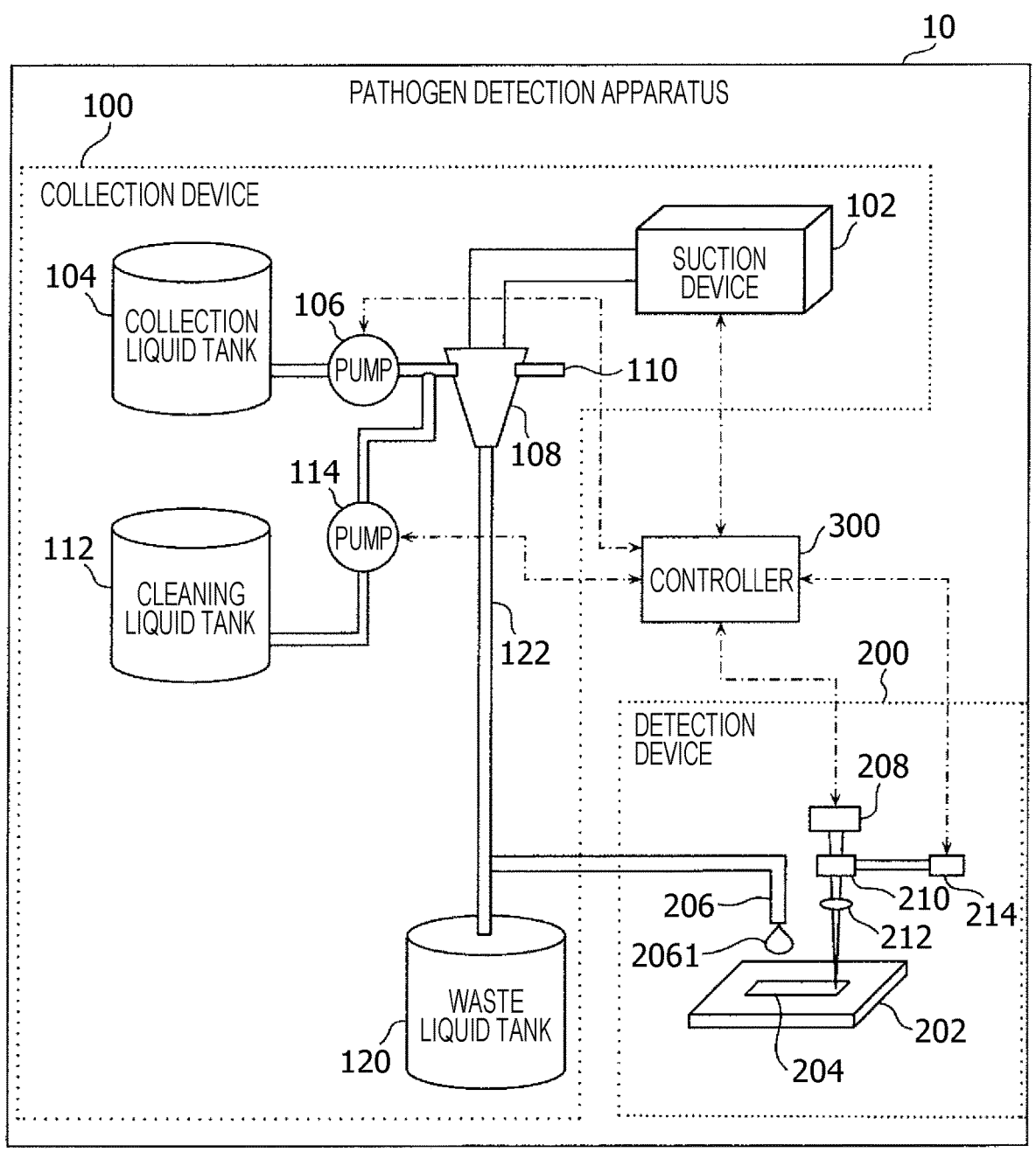
FIG. 1 is a schematic configuration diagram of a pathogen detection apparatus according to an embodiment.

Underlying Knowledge Forming Basis of the Present Disclosure

The inventor has found that the following issues occur regarding the virus collection apparatus described in "Description of the Related Art".

In conventional practice, to prevent the spread of infectious diseases caused by pathogens, nasal mucus, blood, or urine specimens are collected from patients suspected to be infected, and analysis is performed by using the specimens to determine whether or not the patients are infected. For example, regarding influenza that spreads every year, a swab is inserted into the nose of a patient suspected to be infected with an influenza virus, nasal mucus in the nasal cavity is collected as a specimen, and a pathogen such as a virus and/or bacterium in the specimen is detected by using immunochromatography. Such a detection method is applied to a patient suspected to be infected to some extent, and thus it is necessary to collect a specimen from a portion of the suspected patient where a very large quantity of virus is estimated to be present.

On the other hand, collecting of viruses suspended in the air is desired to prevent the spread of infectious diseases, and there is an apparatus for collecting viruses in the air as disclosed in Japanese Unexamined Patent Application Publication No. 2012-52866.

However, in the case of collecting viruses in the air, unlike in the case of collecting a specimen directly from a patient, the aim is to detect the quantity of virus in a space to calculate the risk of becoming infected with a virus in the space. Thus, it is necessary to regularly perform virus detection both in the cases where the quantity of virus is large and small.

Meanwhile, an influenza virus is not constantly detected every day even in the season when influenza spreads. Thus, if measurement is continuously performed at constant intervals or at a high frequency when a virus, such as an influenza virus, is not detected, consumables used for detection or energy for operating an apparatus is wasted. In other words, if detection is continuously performed at a constant frequency, consumables related to the detection or energy is uniformly consumed even if the quantity of virus is small, and thus the consumables or energy is wasted.

The technique disclosed in Japanese Unexamined Patent Application Publication No. 2012-52866 continuously performs detection regardless of the presence or absence of a pathogen, and thus necessary resources or electric power is wasted when a situation continues in which a pathogen is absent.

To address the above issues, a pathogen detection apparatus according to an aspect of the present disclosure includes a collector that collects a pathogen in air; a reactor that causes the pathogen collected by the collector to react with a labeled substance; a time measurer that measures time from start of reaction in the reactor; a detector that detects a quantity of labeled substance that has reacted with the pathogen; and a controller. The controller calculates a gradient value on the basis of a predetermined time period from the start of reaction measured by the time measurer and the quantity of labeled substance detected by the detector, and determines, on the basis of the gradient value, a time interval to next collection that is to be performed by the collector.

Accordingly, the time interval to the next collection that is to be performed by the collector is determined in accordance with the gradient value, and thus the time period from when a detection is finished to when the next detection is performed is appropriately determined. Thus, a pathogen detection frequency is decreased, and thereby waste of consumables or energy can be reduced.

The detector may include a light irradiator that irradiates the reactor with excitation light, and may detect the quantity of labeled substance on the basis of fluorescence generated by the labeled substance as a result of irradiation with the excitation light.

Accordingly, the quantity of labeled substance is detected by detecting fluorescence, and thus the quantity of labeled substance can be effectively detected.

The detector may detect an intensity of the fluorescence generated by the labeled substance as a result of irradiation with the excitation light, and may detect the quantity of labeled substance on the basis of the detected intensity of the fluorescence and chronological changes in attenuation of the intensity of the fluorescence detected by irradiating the labeled substance with the excitation light, the chronological changes being stored in advance.

Accordingly, the quantity of labeled substance is detected on the basis of the intensity of the fluorescence and the chronological changes in attenuation of the fluorescence, and thus the gradient value can be calculated in an early stage after the start of reaction.

The light irradiator may emit the excitation light at predetermined intervals. The detector may detect chronological changes in the quantity of labeled substance. The controller may calculate the gradient value by dividing, by the predetermined time period, a result obtained by subtracting a first quantity of labeled substance from a second quantity of labeled substance in the chronological changes, the first quantity of labeled substance being detected through irradiation with the excitation light at a first timing that is the start of reaction, the second quantity of labeled substance being detected through irradiation with the excitation light at a second timing that is the predetermined time period after the first timing.

Accordingly, the second quantity of labeled substance can be appropriately detected, and the gradient value in an early stage after the start of reaction can be accurately calculated.

The collector may collect a first pathogen at a first time, the first pathogen being the pathogen. The collector may collect a second pathogen at a second time, may collect a third pathogen at a third time, and may not collect a pathogen between the second time and the third time except for the first time, the second time being before the first time, the third time being after the first time. The time interval may be an interval between the first time and the third time. In a case where the gradient value related to the first pathogen is smaller than a predetermined threshold value, the controller may set the time interval to be longer than an interval between the second time and the first time.

Accordingly, in a case where the gradient value is smaller than the predetermined threshold value, a determination is made that the quantity of pathogen is small, and the time interval to the next pathogen detection is set to be longer. Thus, a pathogen detection frequency can be decreased in a case where the quantity of pathogen is small.

The collector may collect a first pathogen at a first time, the first pathogen being the pathogen. The collector may collect a second pathogen at a second time, may collect a third pathogen at a third time, and may not collect a pathogen between the second time and the third time except for the first time, the second time being before the first time, the third time being after the first time. The time interval may be an interval between the first time and the third time. In a case where the gradient value related to the first pathogen is larger than or equal to a predetermined threshold value, the controller may set the time interval to be shorter than an interval between the second time and the first time.

Accordingly, in a case where the gradient value is larger than or equal to the predetermined threshold value, a determination is made that the quantity of pathogen is large, and the time interval to the next pathogen detection is set to be shorter. Thus, a pathogen detection frequency can be increased in a case where the quantity of pathogen is large, and a situation can be prevented from occurring where detection is not performed for a long time despite the presence of a pathogen.

The controller may cause the detector to continue detecting the quantity of labeled substance in a case where the gradient value is larger than or equal to a predetermined threshold value, and may cause the detector to discontinue detecting the quantity of labeled substance in a case where the gradient value is smaller than the predetermined threshold value.

Accordingly, in a case where the gradient value is larger than or equal to the predetermined threshold value, a determination is made that the quantity of pathogen is large, and the quantity of pathogen can be estimated by using a result obtained by continuing the detection of the quantity of labeled substance. In a case where the gradient value is smaller than the predetermined threshold value, a determination is made that the quantity of pathogen is small and that it is not necessary to estimate the quantity of pathogen, and the detection of the quantity of labeled substance can be discontinued. As a result of the discontinuation, the energy consumption of the pathogen detection apparatus can be reduced.

It should be noted that general or specific embodiments may be implemented as a system, a method, an integrated circuit, a computer program, a computer-readable recording medium such as a CD-ROM, or any selective combination thereof.

Hereinafter, a pathogen detection apparatus and a pathogen detection method that relate to one aspect of the present disclosure will be described in detail with reference to the drawings.

The embodiment described below is one specific example of the present disclosure. The values, shapes, materials, components, arrangement positions and connection styles of the components, steps, order of steps, and so forth described in the following embodiment are merely examples and do not limit the present disclosure. Among the components described in the following embodiment, a component that is not described in an independent claim stating the broadest concept will be described as an optional component.

Embodiment

Overview of Pathogen Detection Apparatus

A pathogen detection apparatus is an apparatus that has a collection function capable of colleting viruses suspended in the air, such as an influenza virus, and a function of detecting a virus by testing an extraction liquid containing the collected viruses. In particular, the detection is performed by using antibodies that bind specifically to virus components contained in the extraction liquid containing the viruses, with use of a function in which antibodies bind specifically to antigens.

FIG. 1 is a schematic configuration diagram of a pathogen detection apparatus 10 according to an embodiment. The pathogen detection apparatus 10 is installed in, for example, a room where people come in and out. As illustrated in FIG. 1, the pathogen detection apparatus 10 includes a collection device 100, a detection device 200, and a controller 300. Hereinafter, the details of the collection device 100, the detection device 200, and the controller 300 will be described.

Configuration of Collection Device

The collection device 100 collects microparticles that may contain viruses in the air and mixes the microparticles into a collection liquid. As illustrated in FIG. 1, the collection device 100 includes a suction device 102, a collection liquid tank 104, a pump 106, a cyclone 108, an air intake port 110, a cleaning liquid tank 112, a pump 114, a waste liquid tank 120, and a liquid channel 122. Hereinafter, the individual components of the collection device 100 will be described.

The suction device 102 sucks in the surrounding atmospheric air through the air intake port 110. Microparticles that may contain viruses suspended in the surrounding atmospheric air are sucked into the cyclone 108 through the air intake port 110 together with the air.

The collection liquid tank 104 is a container for holding a collection liquid for collecting viruses in the air.

The pump 106 supplies the cyclone 108 with the collection liquid in the collection liquid tank 104.

The cyclone 108 is connected to the air intake port 110 and the collection liquid tank 104, and mixes the microparticles that may contain viruses in the air sucked by the suction device 102 through the air intake port 110 and the collection liquid supplied from the collection liquid tank 104 by the pump 106. The cyclone 108 is connected to the detection device 200 via the liquid channel 122. The collection liquid mixed with the microparticles (hereinafter referred to as a specimen) is discharged from the cyclone 108 to the detection device 200 via the liquid channel 122.

The cleaning liquid tank 112 is a container for holding a cleaning liquid for cleaning the cyclone 108 and the liquid channel 122. The cleaning liquid tank 112 is connected to the cyclone 108, and the cleaning liquid in the cleaning liquid tank 112 is supplied to the cyclone 108 by the pump 114.

The waste liquid tank 120 is a container for storing an unnecessary liquid.

The liquid channel 122 is a path for leading a specimen output from the cyclone 108 to the detection device 200.

Figure 2:
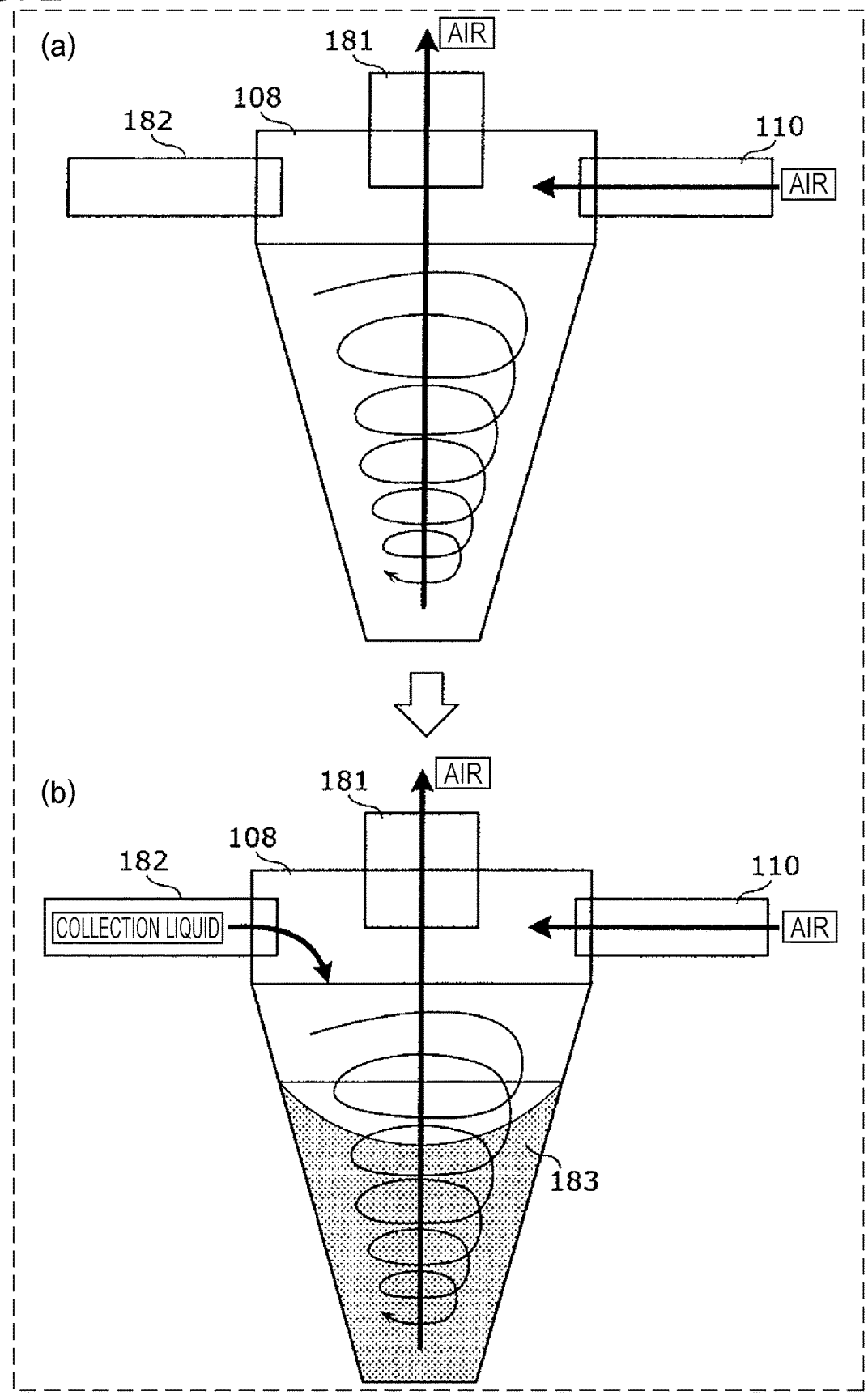
FIG. 2 is a diagram for describing the function of a cyclone according to the embodiment.

FIG. 2 is a diagram for describing the function of the cyclone 108 according to the embodiment.

In the case of collecting viruses suspended in the air, such as an influenza virus, it is necessary to take in a large quantity of air and collect viruses in the taken air into a liquid because it is estimated that only a very small quantity of virus is suspended in the air. Here, the viruses are collected into the liquid to generally perform the above-mentioned binding between antibodies and virus components in the liquid. The liquid may be pure water free of impurities, or a solution prepared by dissolving in pure water a phosphate buffer typically used as a solvent of a biological material, so that the virus components are not degenerated. For example, phosphate buffered saline (PBS), Tris, and the like are available.

The cyclone 108 may be used to take in a large quantity of air. In the cyclone 108, as illustrated in FIG. 2(a), air is sucked through a suction port 181 connected to the suction device 102, and thereby the air is taken into the cyclone 108 through the air intake port 110. The taken air is rotated at a high speed in the cyclone 108. At this time, microparticles contained in the taken air and having a size larger than or equal to a certain size are unable to follow an air flow in the cyclone 108 and are centrifugally blown toward an inner wall surface of the cyclone 108, thereby being separated from the air. The microparticles separated from the air are collected to a lower portion of the cyclone 108.

In this way, the suction into the cyclone 108 causes an influenza virus suspended in the air to enter the cyclone 108 through the air intake port 110 and to be centrifugally blown toward the inner wall surface of the cyclone 108. In a case where the lower portion of the cyclone 108 is filled with a predetermined quantity of collection liquid 183 before starting the suction, an airflow in the cyclone 108 causes the collection liquid 183 to spirally rotate and to rise along the inner wall surface of the cyclone 108 as illustrated in FIG. 2(b), and an influenza virus blown toward the inner wall surface can be captured in the solution. The collection liquid 183 is supplied, for example, from a collection liquid intake port 182 of the cyclone 108 connected to the pump 106 into the cyclone 108.

Configuration of Detection Device

Figure 3:
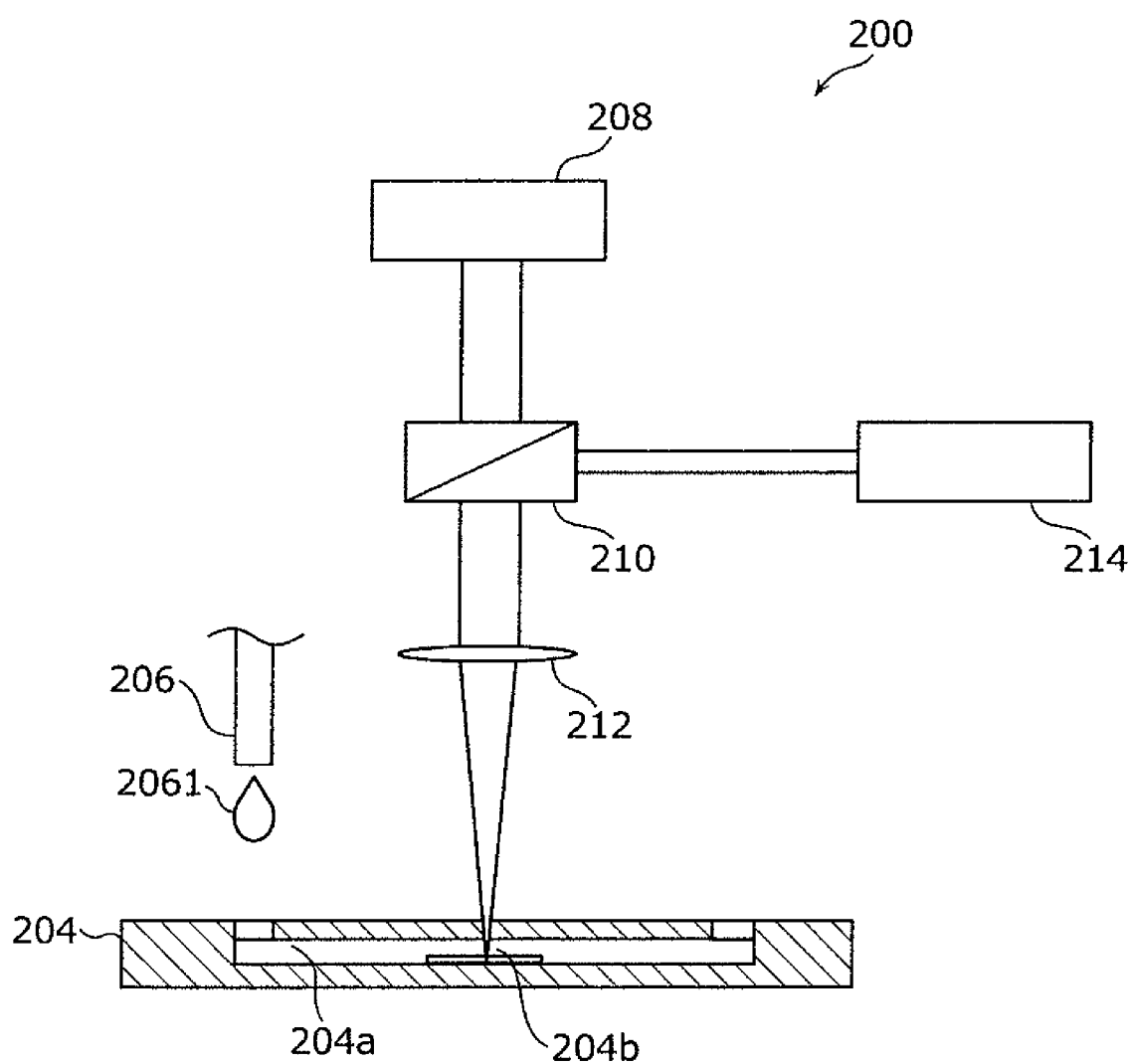
FIG. 3 is a configuration diagram of a detection device according to the embodiment.

The detection device 200 will be described in detail with reference to FIG. 1 and FIG. 3. FIG. 3 is a configuration diagram of the detection device 200 according to the embodiment.

The detection device 200 detects a virus from a collection liquid mixed with microparticles by the collection device 100. As illustrated in FIG. 1 and FIG. 3, the detection device 200 includes a sensor device 202, a loading unit 206, a light source 208, a beam splitter 210, a lens 212, and a detecting unit 214. Hereinafter, the individual components of the detection device 200 will be described.

The sensor device 202 includes a sensor cell 204. In FIG. 1, the sensor device 202 includes the single sensor cell 204. Alternatively, the sensor device 202 may include sensor cells.

In the present embodiment, the sensor device 202 is capable of detecting viruses in a concentration range from 0.1 pM to 100 nM. In the present embodiment, a surface-enhanced fluorescence method is used to optically detect the quantity of virus.

The sensor cell 204 generates surface plasmons when irradiated with excitation light, thereby enhancing fluorescence emitted by a fluorescent substance bound to a virus. As illustrated in FIG. 3, the sensor cell 204 includes a channel 204a and a detection region 204b.

The channel 204a is a path for leading a sample liquid 2061 dropped by the loading unit 206 to the detection region 204b.

The detection region 204b is a region for optically detecting a virus by using surface plasmons. A metal microstructure is disposed in the detection region 204b, where surface plasmons are generated when irradiated with excitation light emitted by the light source 208. In addition, first VHH antibodies are immobilized on the metal microstructure. The first VHH antibodies are immobilized antibodies that bind specifically to a virus. The details of the detection region 204b will be described below with reference to FIG. 3 and FIG. 4.

The loading unit 206 loads second VHH antibodies and a specimen to the sensor cell 204. Specifically, the loading unit 206 drops the sample liquid 2061 containing the second VHH antibodies and the specimen onto the sensor cell 204. The second VHH antibodies are labeled antibodies labeled with fluorescent substances. The specimen is a liquid that may contain a virus and is, in the present embodiment, a collection liquid discharged by the cyclone 108.

If the specimen contains a virus, the virus binds to the metal microstructure via the first VHH antibodies. At this time, the virus also binds to the second VHH antibodies labeled with fluorescent substances. In other words, the second VHH antibodies, which are labeled antibodies labeled with fluorescent substances, bind to the metal microstructure via the virus and the first VHH antibodies. When the metal microstructure is irradiated with light in this state, the fluorescent substances indirectly bound to the virus emit fluorescence, and the fluorescence is enhanced by surface plasmons. Hereinafter, the fluorescence enhanced by surface plasmons will be referred to as surface-enhanced fluorescence.

The light source 208 is an example of a light irradiator that irradiates the sensor cell 204 with excitation light. Any device according to the related art can be used as the light source 208 without particular limitation. For example, a laser, such as a semiconductor laser or a gas laser, can be used as the light source 208. The light source 208 may emit excitation light whose wavelength has a small interaction with a substance contained in a virus (for example, 400 nm to 2000 nm). Furthermore, the wavelength of the excitation light may be 600 nm to 850 nm that can be used by a semiconductor laser.

The beam splitter 210 separates the surface-enhanced fluorescence generated in the detection region 204b from the excitation light emitted by the light source 208. Specifically, the beam splitter 210 allows the excitation light from the light source 208 to pass therethrough, separates the surface-enhanced fluorescence generated in the sensor cell 204 from the excitation light, and leads the surface-enhanced fluorescence to the detecting unit 214.

The lens 212 condenses the excitation light emitted by the light source 208 and passed through the beam splitter 210 onto the detection region 204b.

The detecting unit 214 divides the surface-enhanced fluorescence led by the beam splitter 210 and detects light in a specific wavelength range, thereby outputting an electric signal corresponding to the quantity of virus in the specimen. Any device capable of detecting light in the specific wavelength range according to the related art can be used as the detecting unit 214 without particular limitation. For example, an interference filter that allows a specific wavelength range to pass therethrough to divide light, a Czerny spectrometer that divides light by using a diffraction grating, an Echelle spectrometer, or the like can be used as the detecting unit 214. Furthermore, the detecting unit 214 may include a notch filter for removing the excitation light from the light source 208, or a longpass filter that is capable of blocking the excitation light from the light source 208 and allowing the surface-enhanced fluorescence generated by the sensor cell 204 to pass therethrough.

Configuration of Controller

The controller 300 controls the operation of the entire pathogen detection apparatus 10. Specifically, the controller 300 controls the collection device 100 and the detection device 200.

More specifically, the controller 300 controls the start of measurement, causes the suction device 102 to start sucking the surrounding air, and causes the pump 106 to supply a collection liquid from the collection liquid tank 104 to the cyclone 108. Accordingly, the collection liquid is mixed with microparticles in the cyclone 108, and a specimen is supplied from the cyclone 108 to the detection device 200. Furthermore, the controller 300 causes the light source 208 to emit light and causes the detecting unit 214 to detect surface-enhanced fluorescence.

For example, the controller 300 is capable of controlling each pump to supply a predetermined volume of sample liquid to the detection device 200 under a preset condition on the basis of an input parameter. Furthermore, the controller 300 may have a time measurement function, and may generate and store information on the time taken for each operation. In addition, the controller 300 may receive a time measurement value from the detection device 200, and may calculate a chronological change in the concentration of viruses suspended in the air on the basis of the time measurement value and time information.

The controller 300 is formed of, for example, one or more dedicated electronic circuits. The one or more dedicated electronic circuits may be integrated on one chip or may be individually formed on chips. Alternatively, the controller 300 may be formed of, instead of the one or more dedicated electronic circuits, a general-purpose processor (not illustrated) and a memory (not illustrated) storing a software program or instruction. In this case, the processor functions as the controller 300 when the software program or instruction is executed.

Next, a detection method for the detection device 200 will be described in detail.

One influenza virus contains virus components including about 1000 nucleoprotein (NP) molecules. Thus, to detect a larger number of NP molecules to facilitate a detection, an influenza virus may be crushed to extract the NP molecules contained in the influenza virus. To crush the influenza virus, a surface-active agent is injected to break a membrane substance that covers the surface of the influenza virus, and the NP molecules therein are extracted. As the surface-active agent used for crush, Tween 20, Triton X, Sarkosyl, and the like are available. Alternatively, a captured virus may be caused to react with an antibody for detection without crushing the virus.

In general, detection of a biological material is performed by using an antigen-antibody reaction in which an antigen is caused to react with an antibody. Here, the antigen is an influenza virus or NP, which is a component contained in the influenza virus. The antibody reacts specifically with the antigen and binds to the antigen. Hereinafter, a detection method using an antigen-antibody reaction will be described in detail.

Figure 4:
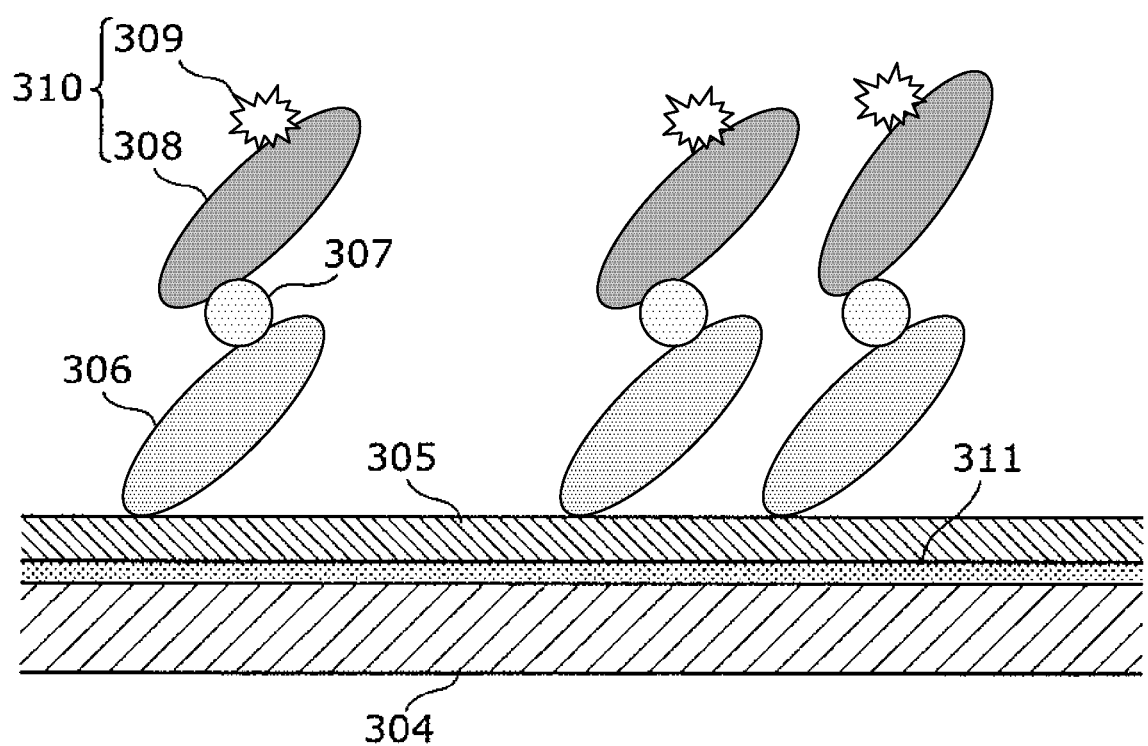
FIG. 4 is a diagram for describing the details of an antigen-antibody reaction.
Figure 5:
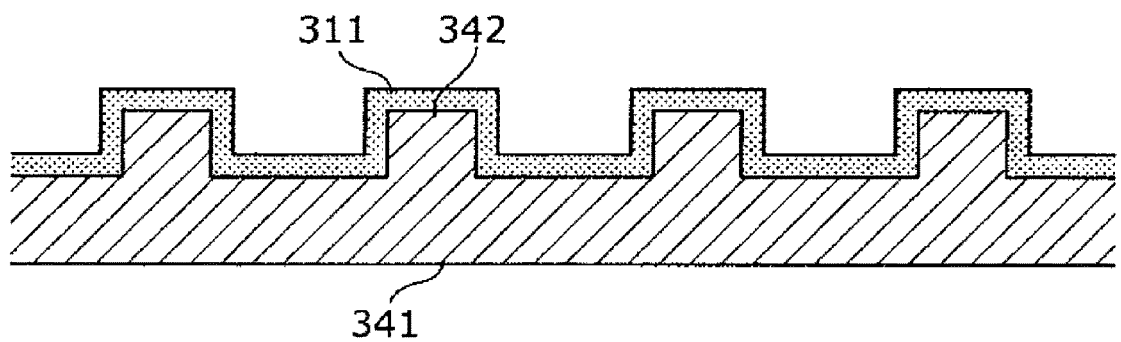
FIG. 5 is a diagram illustrating an example of a substrate structure in the case of using surface plasmon resonance.

A description will be given with reference to FIG. 4. FIG. 4 is a diagram for describing the details of an antigen-antibody reaction.

First, on a surface of a substrate 304 disposed in the above-described sensor cell 204, first antibodies 306 are formed which bind to a virus or NP as a virus component serving as an antigen. The first antibodies 306 play a role in capturing NP molecules 307 or the like to the surface of the substrate 304. The first antibodies 306 are, for example, IgG antibodies. Among IgG antibodies, those having an ability to bind specifically to an influenza virus or NP as an influenza virus component may be used. The first antibodies 306 are also referred to as capture antibodies. The surface of the substrate 304 is modified with a self-assembled monolayer (SAM) 305 to cause the inorganic substrate and the organic antibodies to bind to each other. The first antibodies 306 are immobilized on the surface of the substrate 304 via the SAM 305.

The SAM 305 is formed on a surface of a gold single-crystal thin layer 311 formed on the surface of the substrate 304. Accordingly, the SAM 305 is a closely-packed and regularly-oriented monolayer formed by the Au—S—R bond resulting from alkanethiol (R—SH) bound to the single-crystal thin layer 311. In this way, in the antigen-antibody reaction, the first antibodies 306 are caused to bind to the SAM 305 formed on the surface of the substrate 304.

Subsequently, a solution containing the NP molecules 307, which are antigens, is injected to the first antibodies 306 immobilized on the surface of the substrate 304 via the SAM 305. In other words, a solution containing the NP molecules 307 is injected to the detection region 204b of the sensor cell 204. At this time, the first antibodies 306 start binding to the NP molecules 307 as antigens, and then the number of bonds increases as time elapses. While the number of bonds increases, dissociation occurs. Accordingly, the first antibodies 306 and the NP molecules 307 repeat binding and dissociation to reach an equilibrium state.

Subsequently, a solution containing second antibodies 308 is injected to the detection region 204b of the sensor cell 204. Like the first antibodies 306, the second antibodies 308 are, for example, IgG antibodies capable of binding to an influenza virus or the NP molecules 307, which are influenza virus components. A labeled substance 309 that emits a signal for performing detection is bound to each second antibody 308 in advance. The labeled substance 309 may be, for example, a substance that emits fluorescence when being irradiated with laser light having a predetermined wavelength. The labeled substance 309 is, for example, DyLight 800 that emits fluorescence having a wavelength of 800 nm when being irradiated with laser light having a wavelength of 785 nm. The second antibody 308 to which the labeled substance 309 is bound is also referred to as a labeled antibody 310.

In a case where a virus is present in the air, the virus is captured into the collection liquid 183 in the cyclone 108 when the cycle 108 is operated. The captured virus is crushed, and thereby the NP molecules 307 in the virus are extracted. A solution containing the NP molecules 307 obtained accordingly is injected to the detection region 204*b* of the sensor cell 204. In other words, when a solution containing the NP molecules 307 is injected onto the SAM 305 on the substrate 304, the NP molecules 307 bind to the first antibodies 306 serving as capture antibodies formed on the surface of the substrate 304 via the SAM 305. Furthermore, when a solution containing the second antibodies 308 serving as labeled antibodies each bound to the labeled substance 309 that emits fluorescence is injected, the second antibodies 308 bind to the NP molecules 307, which are antigens bound to the first antibodies 306. The binding of the first antibodies 306, the NP molecules 307 as antigens, and the second antibodies 308 is referred to as sandwich assay. The solution in the detection region 204*b* that has undergone sandwich assay is irradiated with laser light, which is excitation light for exciting fluorescence in the labeled substances 309 bound to the second antibodies 308, and the excited fluorescence is measured to obtain a signal to be detected.

In the detection device 200, the light source 208 repeatedly irradiates the detection region 204*b* with laser light at predetermined intervals, and the detecting unit 214 repeatedly detects, at predetermined intervals, fluorescence excited from the labeled substances 309 in response to irradiation with the laser light. The repeated irradiation with laser light increases the intensity of emitted fluorescence as the binding of the first antibodies 306, the NP molecules 307, and the labeled antibodies 310 progresses. When a solution containing the labeled antibodies 310 is injected, a labeled antibody 310 that does not bind to any NP molecule 307 is suspended in a liquid layer. The number of bonds between the NP molecules 307 and the labeled antibodies 310 changes in accordance with the amount of solution injected and/or the thickness of the liquid layer held in the sensor cell 204.

In an early stage after the solution of the labeled antibodies 310 is injected, the number of bonds between the NP molecules 307 and the labeled antibodies 310 gradually increases. When the intensity of laser light that excites fluorescence in the labeled substances 309 of the labeled antibodies 310 is increased, the labeled substance 309 of a suspended labeled antibody 310 that is not bound to any NP molecule 307 emits light. If the fluorescence emitted at this time is detected, it is not possible to accurately detect the NP molecules 307, and thus it is not possible to indiscriminately increase the intensity of laser light. On the other hand, when the quantity of virus in the air is very small, a small quantity of NP molecule 307 is obtained, and thus the intensity of excitation light may be increased.

To increase the strengths of signals from the labeled antibodies 310 bound to the NP molecules 307 near the surface of the substrate 304, surface plasmon resonance is used. FIG. 5 is a diagram illustrating an example of a substrate structure in the case of using surface plasmon resonance.

Surface plasmon resonance has traditionally been known. For example, as illustrated in FIG. 5, nano-size protrusions 342 are formed on a surface of a substrate 341, and a single-crystal thin layer 311 made of Au or the like is formed on the surfaces of the protrusions 342, and thereby a strong-electromagnetic-field region is formed near the surface of the substrate 341. The strong-electromagnetic-field region is formed very close to the surface of the substrate 341, which enables the labeled substance 309 emitting a signal of the second antibody 308 bound to the NP molecule 307 to emit light whose intensity is higher than the light emitted by the labeled substance 309 of the labeled antibody 310 that is suspended away from the surface of the substrate 341 and is not bound to the NP molecule 307. The combination of surface plasmon resonance and sandwich assay makes it possible to effectively detect a very small quantity of virus in the air and to effectively detect a transient state where the signal strength gradually increases in an early stage after the second antibodies 308 and the NP molecules 307 start binding to each other.

However, organic fluorescent substances are often used as the labeled substances 309 of the labeled antibodies 310. The organic fluorescent substances have a property that the intensity of excited fluorescence gradually decreases when being continuously irradiated with excitation light. This property is referred to as fluorescence deactivation.

It is considered that, if the second antibodies 308 are irradiated with excitation light from when a solution containing the second antibodies 308 is injected after the first antibodies 306 and the NP molecules 307 bind to each other, and then excited fluorescence is detected, the intensity of the detected fluorescence increases because the NP molecules 307 and the labeled antibodies 310 gradually bind to each other. However, as indicated by the chain line representing "observation value" in the graph in FIG. 6, fluorescence deactivation actually occurs in which the intensity of fluorescence from the labeled substances 309 decreases due to continuous irradiation with excitation light at the same place. Thus, the amount of decrease in intensity of fluorescence resulting from fluorescence deactivation exceeds the amount of increase in intensity of fluorescence resulting from the binding at a certain time point, and the intensity of fluorescence that is detected gradually decreases as time elapses.

Thus, as a result of grasping in advance the ratio of decrease in intensity of fluorescence and correcting a fluorescence deactivation component of the detected intensity of fluorescence, a signal that is to be originally obtained as an increase from the reaction can be calculated. In the graph in FIG. 6, the broken line representing "fluorescence deactivation" indicates chronological changes in the value obtained by dividing, by an initial value, a measurement value of fluorescence intensity actually measured at constant time intervals in a state where the labeled substances 309 used for sandwich assay are directly immobilized on the surface the single-crystal thin layer 311 formed on the surface of the substrate 304 of the detection device 200 and are periodically irradiated with excitation light by using the light source 208. The initial value may be, for example, a fluorescence intensity measured at the time when the NP molecules 307 and the labeled substances 309 are loaded to the sensor cell 204.

It is understood from the broken line representing "fluorescence deactivation" that continuous irradiation with excitation light at the same place causes a decrease in fluorescence intensity. The chronological changes in deactivation (or attenuation) of the fluorescence intensity detected by continuously irradiating the labeled substances 309 with laser light are measured in this manner and stored in a memory or the like.

Figure 6:
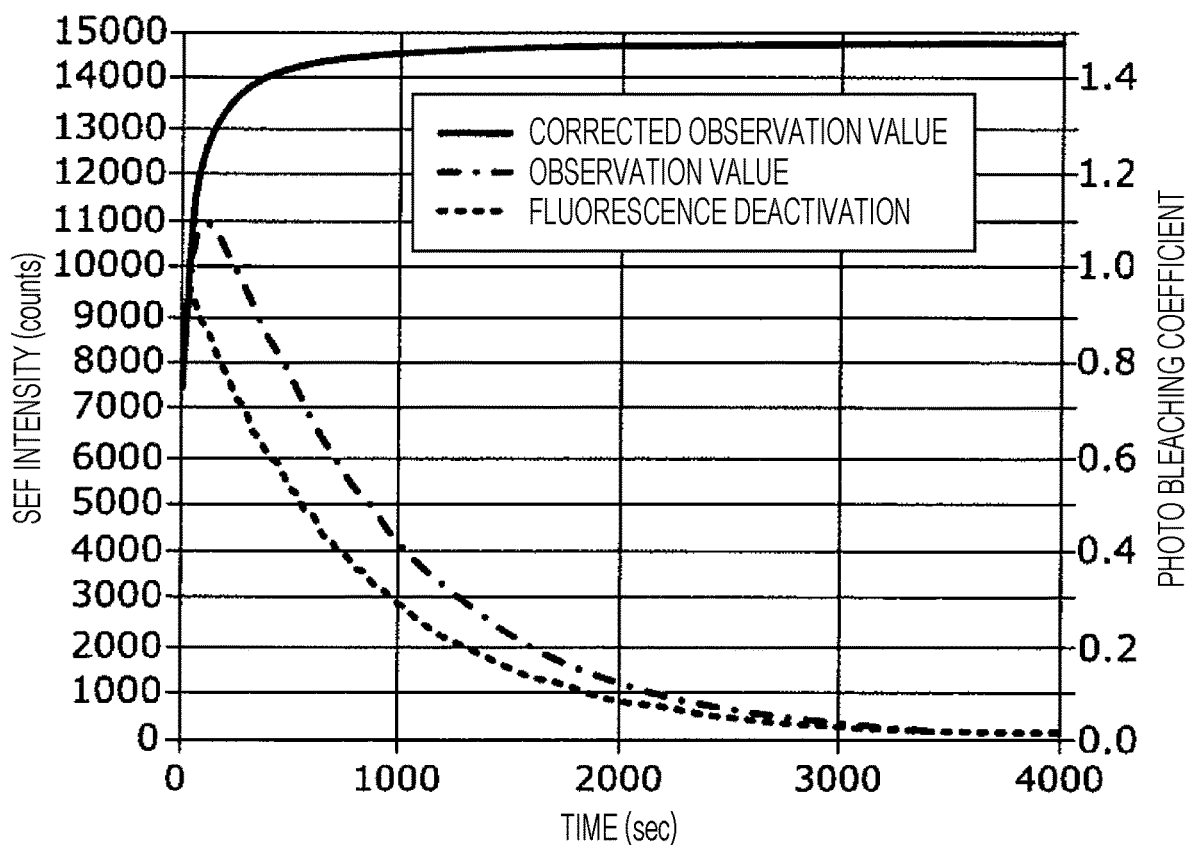
FIG. 6 is a graph illustrating chronological changes in observation value, fluorescence deactivation, and corrected value.

In the graph in FIG. 6, the chain line representing "observation value" indicates chronological changes in the measurement value of the fluorescence intensity measured at constant time intervals while periodically emitting excitation light after the NP molecules 307 are bound to the first antibodies 306 immobilized to, via the SAM 305, the surface of the single-crystal thin layer 311 formed on the surface of the substrate 304 and the labeled antibodies 310 are injected. It is understood from the chain line representing "observation value" that the fluorescence intensity that is detected decreases as time elapses.

In the graph in FIG. 6, the solid line representing "corrected observation value" indicates chronological changes in the corrected value obtained by correcting the chronological changes in the fluorescence intensity indicated by the chain line representing "observation value" on the basis of the chronological changes in the fluorescence intensity indicated by the broken line representing "fluorescence deactivation". Approximately, the solid line representing "corrected observation value" can be obtained by dividing, at each time from the start of measurement, the fluorescence intensity indicated by the chain line "observation value" at the time by a coefficient that is based on the broken line representing "fluorescence deactivation" at the time. In this way, the fluorescence deactivation component is corrected in the solid line representing "corrected observation value". Thus, the collected observation value corresponds to the intensity of fluorescence emitted by the labeled substances 309 of the labeled antibodies 310 that increases as the number of NP molecules 307 bound to the labeled antibodies 310 gradually increases in accordance with the progress of the antigen-antibody reaction. The coefficient that is based on the broken line representing "fluorescence deactivation" may be a value obtained by multiplying a value obtained from the broken line representing "fluorescence deactivation" by a predetermined real number.

In a case where a virus is absent in the air, the corrected observation value does not increase as time elapses.

Next, the functional configuration of the pathogen detection apparatus 10 will be described.

Figure 7:
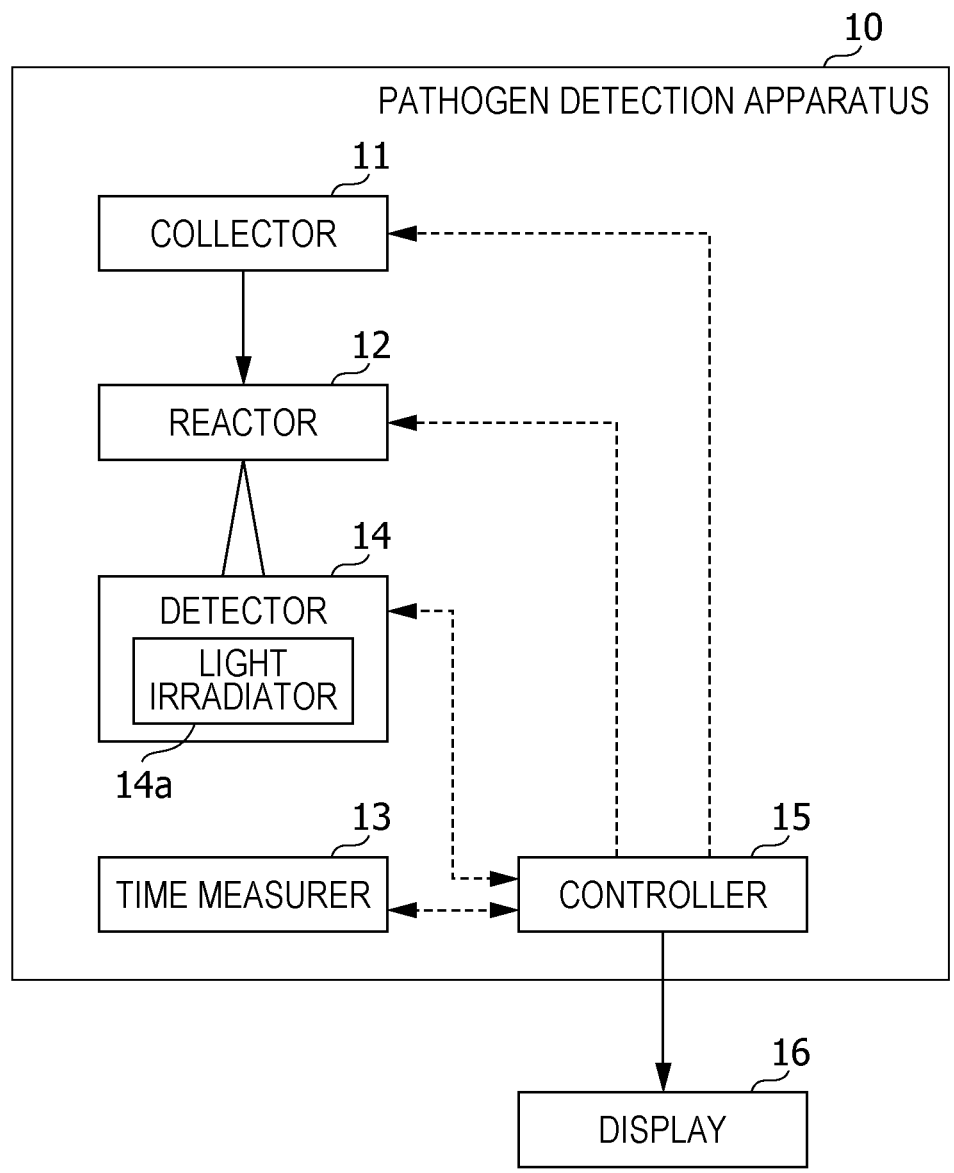
FIG. 7 is a block diagram illustrating an example of the functional configuration of the pathogen detection apparatus according to the embodiment.

FIG. 7 is a block diagram illustrating an example of the functional configuration of the pathogen detection apparatus 10 according to the embodiment.

As illustrated in FIG. 7, the pathogen detection apparatus 10 includes a collector 11, a reactor 12, a time measurer 13, a detector 14, and a controller 15. The pathogen detection apparatus 10 may be connected to a display 16 and may cause the display 16 to display a detection result or a notification based on the detection result.

The collector 11 collects a pathogen in the air. The collector 11 may collect a pathogen in the air at predetermined time intervals. When the time to start collecting a pathogen this time is represented by T1 and the time to start collecting a pathogen next time is represented by T2, the time interval=T2−T1. The pathogen is a virus, for example, an influenza virus. The collector 11 is implemented by, for example, the collection device 100.

The reactor 12 causes the pathogen collected by the collector 11 to react with a labeled substance. The reactor 12 causes the NP molecules 307 of the pathogen to react with the labeled substances 309. For example, the reactor 12 causes the first antibodies 306, the NP molecules 307, and the second antibodies 308 bound to the labeled substances 309 to react with each other, thereby causing them to bind to each other. The reaction in the reactor 12 is not limited to a reaction using surface plasmon resonance. Any reaction may be performed as long as the labeled substances 309 are caused to bind to the pathogen. The reactor 12 is implemented by, for example, the sensor cell 204 of the detection device 200.

The time measurer 13 measures time from the start of the reaction in the reactor 12. The time measurer 13 is implemented by, for example, the controller 300. The reaction start time point may be, for example, the time point at which the NP molecules 307 of the pathogen and the labeled substances 309 are loaded to the sensor cell 204.

The detector 14 detects the quantity of labeled substance, that is, the labeled substances 309 that have reacted with the pathogen. The detector 14 includes a light irradiator 14a that irradiates the reactor 12 with excitation light, and detects the quantity of labeled substance on the basis of fluorescence generated by the labeled substances 309 as a result of irradiation with the excitation light. The detector 14 detects the intensity of the fluorescence generated by the labeled substances 309 as a result of irradiation with the excitation light, and detects the quantity of labeled substance on the basis of the detected intensity of the fluorescence and chronological changes in attenuation of the intensity of the fluorescence detected by irradiating the labeled substances 309 with the excitation light, the chronological changes being stored in advance. In other words, the detector 14 detects the quantity of labeled substance by correcting the detected intensity of fluorescence in the manner described above with reference to FIG. 6. The light irradiator 14a emits excitation light at predetermined intervals. The detector 14 detects chronological changes in the quantity of labeled substance.

The detector 14 is implemented by, for example, the detection device 200, the controller 300, the light source 208, and the like. The correction of the intensity of fluorescence in the detector 14 may be performed by, for example, the detection device 200 or the controller 300. The light irradiator 14a is implemented by the light source 208.

The controller 15 calculates a gradient value (hereinafter also referred to as a concentration gradient) on the basis of a predetermined time period from the start of reaction measured by the time measurer 13 and the quantity of labeled substance detected by the detector 14, and determines, on the basis of the gradient value, the time interval to next collection that is to be performed by the collector 11.

For example, the controller 15 may determine that a virus is present in a case where the gradient value of chronological changes in the quantity of labeled substance detected by the detector 14 is larger than or equal to a predetermined threshold value, and may determine that a virus is absent in a case where the gradient value is smaller than the predetermined threshold value. For example, about 10 nmol/L of NP solution was caused to bind to the first antibodies 306 serving as capture antibodies and then the labeled antibodies 310 having DyLight 800 serving as labeled substances were caused to bind thereto to obtain a sample, which was irradiated with laser light having a wavelength of 785 nm to excite the labeled substances 309. Regarding the intensity of fluorescence measured in this case, the gradient value of chronological changes in about first 20 seconds was 400 counts per second. The "counts" may indicate the number of photons. In this way, whether a virus is present or absent can be determined on the basis of the degree of a slope indicating chronological changes in the detected fluorescence intensity, that is, a gradient value, in a short time period of 20 to 30 seconds, for example, from the start of measurement.

The controller 15 is implemented by, for example, the controller 300.

Figure 8:
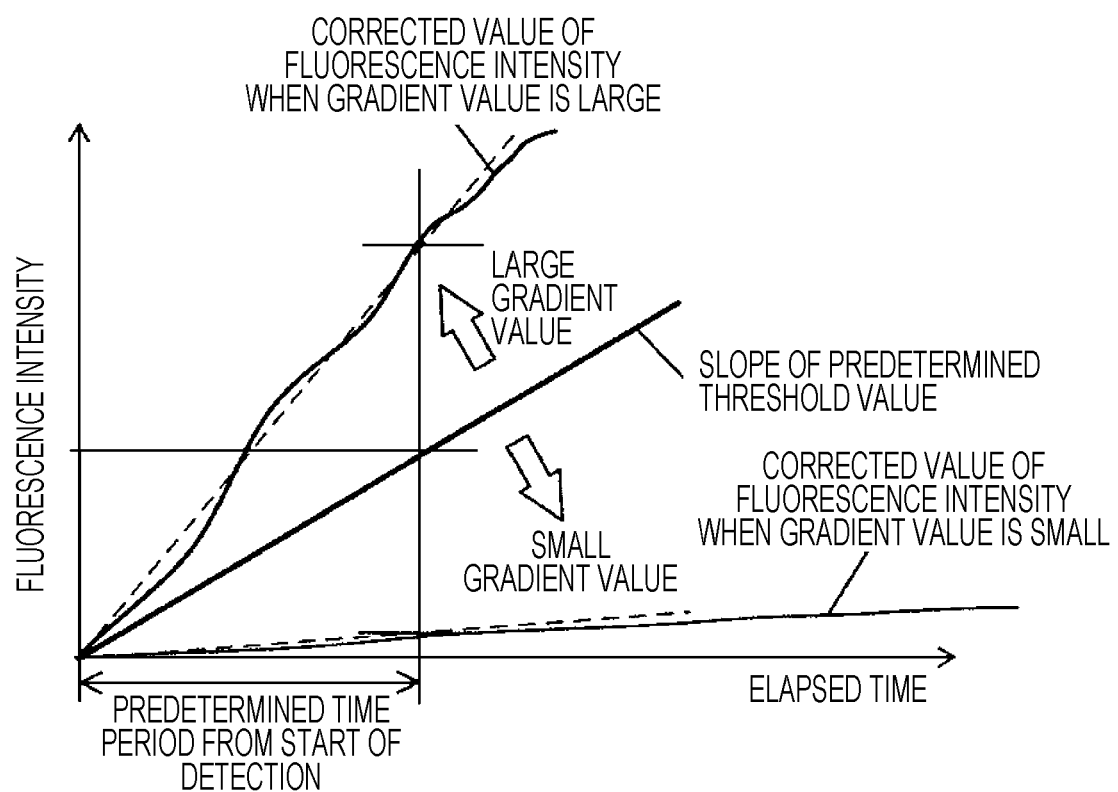
FIG. 8 is a diagram illustrating the relationship between chronological changes in fluorescence intensity from the start of measurement and a predetermined threshold value.

Now, a detailed description will be given of, with reference to FIG. 8, a method for determining the presence or absence of an influenza virus in accordance with whether or not the gradient value of initial chronological changes in fluorescence intensity is smaller than a predetermined threshold value. FIG. 8 is a diagram illustrating the relationship between chronological changes in fluorescence intensity from the start of measurement and a predetermined threshold value. In FIG. 8, the horizontal axis represents the time elapsed from the start of detection of the fluorescence intensity, and the vertical axis represents the corrected value obtained by correcting chronological changes in the detected fluorescence intensity. In the time scale illustrated in FIG. 8, a reaction start time, an irradiation start time, and a detection start time may be regarded as identical to each other.

In a case where a virus is absent in the space, the slope of chronological changes in the corrected value of the fluorescence intensity is ideally zero. However, the slope may have various forms, for example, the slope may represent a slight increase or a slight decrease in accordance with an influence of noise and/or measurement errors, the slope may represent a decrease in a very short time period after the start of measurement and then represent an increase, vice versa, or the slope may repeatedly represent an increase and a decrease and then continuously represent an increase.

Thus, the controller 15 may regard the gradient value as a slope between an initial value of a corrected value of the fluorescence intensity and a corrected value after a predetermined time period from the start of detection. For example, the controller 15 calculates the gradient value by dividing the difference between the initial value and a corrected value after 20 seconds in chronological changes in the corrected value of the detected fluorescence intensity by 20 seconds. In other words, the controller 15 calculates the gradient value by dividing, by a predetermined time period, a result obtained by subtracting a first quantity of labeled substance from a second quantity of labeled substance in chronological changes. The first quantity of labeled substance is detected through irradiation with excitation light at a first timing that is the start of detection (i.e., the start of reaction), and the second quantity of labeled substance is detected through irradiation with excitation light at a second timing that is the predetermined time period after the first timing.

Figure 9:
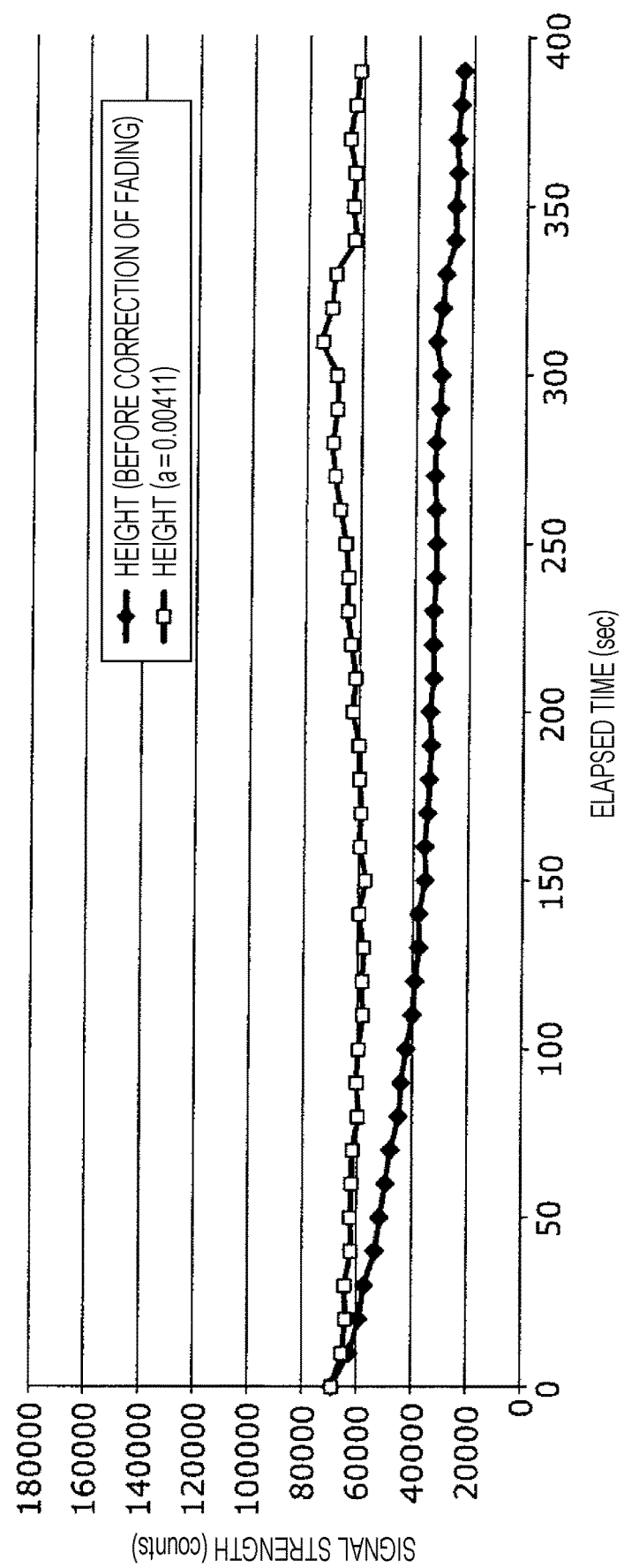
FIG. 9 is a graph illustrating an example of a case where the gradient value of chronological changes in a corrected value is smaller than a predetermined threshold value when the predetermined threshold value is 150 counts per second.

FIG. 9 is a graph illustrating an example of a case where the gradient value of chronological changes in the corrected value is smaller than a predetermined threshold value when the predetermined threshold value is 150 counts per second.

In this case where the gradient value is smaller than the predetermined threshold value, the controller 15 may determine that a virus is absent in the target space and may immediately discontinue the measurement. In this case, the controller 15 may set a time interval at which detection is repeated next time and thereafter to a time interval longer than the current time interval. In a case where no virus is detected continuously, the controller 15 may set the longest measurement interval to 2 hours or half a day.

Figure 10:
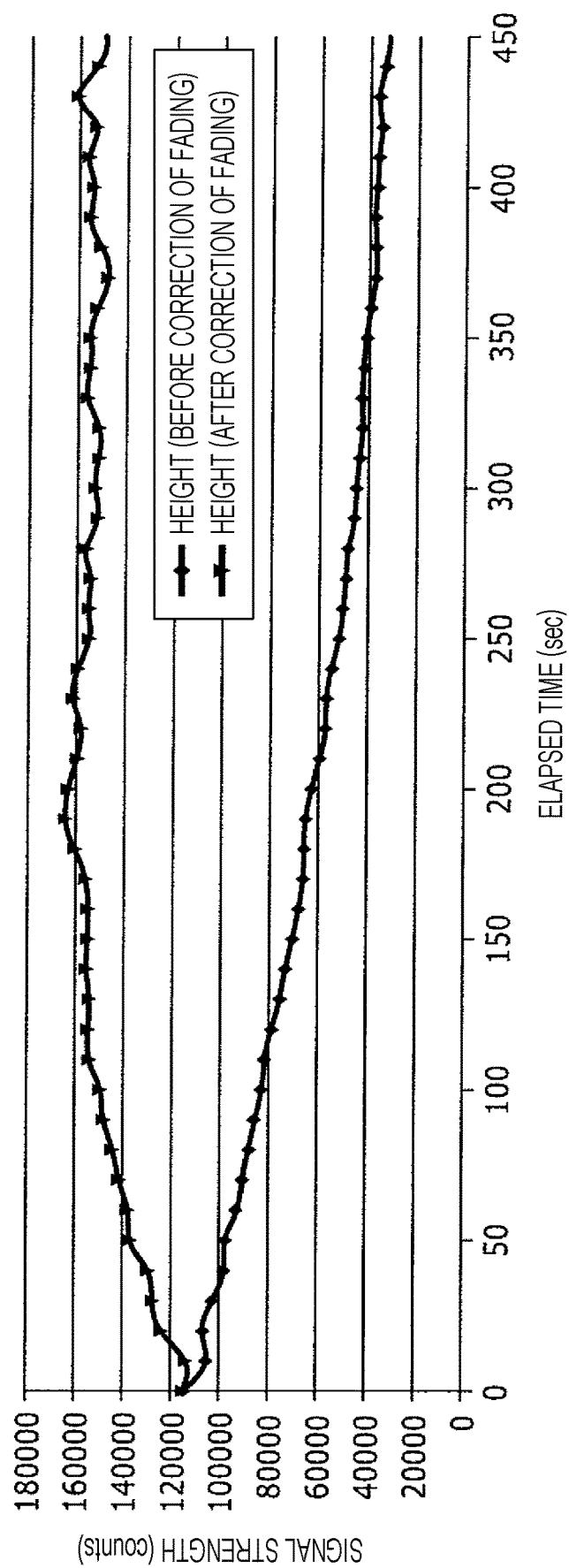
FIG. 10 is a graph illustrating an example of a case where the gradient value of chronological changes in a corrected value is larger than or equal to a predetermined threshold value.

FIG. 10 is a graph illustrating an example of a case where the gradient value of chronological changes in the corrected value is larger than or equal to a predetermined threshold value. In this case where the gradient value is larger than or equal to the predetermined threshold value, the controller 15 may determine that a virus is present in the air, may calculate a virus concentration, and may issue an indicator of the possibility of infection on the basis of the calculated virus concentration.

In other words, for example, the controller 15 determines whether or not the gradient value is smaller than the predetermined threshold value, and, in a case where the gradient value is smaller than the predetermined threshold value, the controller 15 may set the time interval to the next collection to be performed by the collector 11 to be longer than the time interval from the time at which the collector 11 performed collection last time to the time at which the collector 11 performed collection this time. On the other hand, in a case where the gradient value is larger than or equal to the predetermined threshold value, the controller 15 may set the time interval to be shorter than the time interval from the time at which the collector 11 performed collection last time to the time at which the collector 11 performed collection this time. In addition, in a case where the gradient value is larger than or equal to the predetermined threshold value, the controller 15 may cause the detector 14 to continue detecting the quantity of labeled substance, whereas in a case where the gradient value is smaller than the predetermined threshold value, the controller 15 may cause the detector 14 to discontinue detecting the quantity of labeled substance.

Operation of Pathogen Detection Apparatus

Hereinafter, a pathogen detection method for the pathogen detection apparatus 10 will be described.

Figure 11:
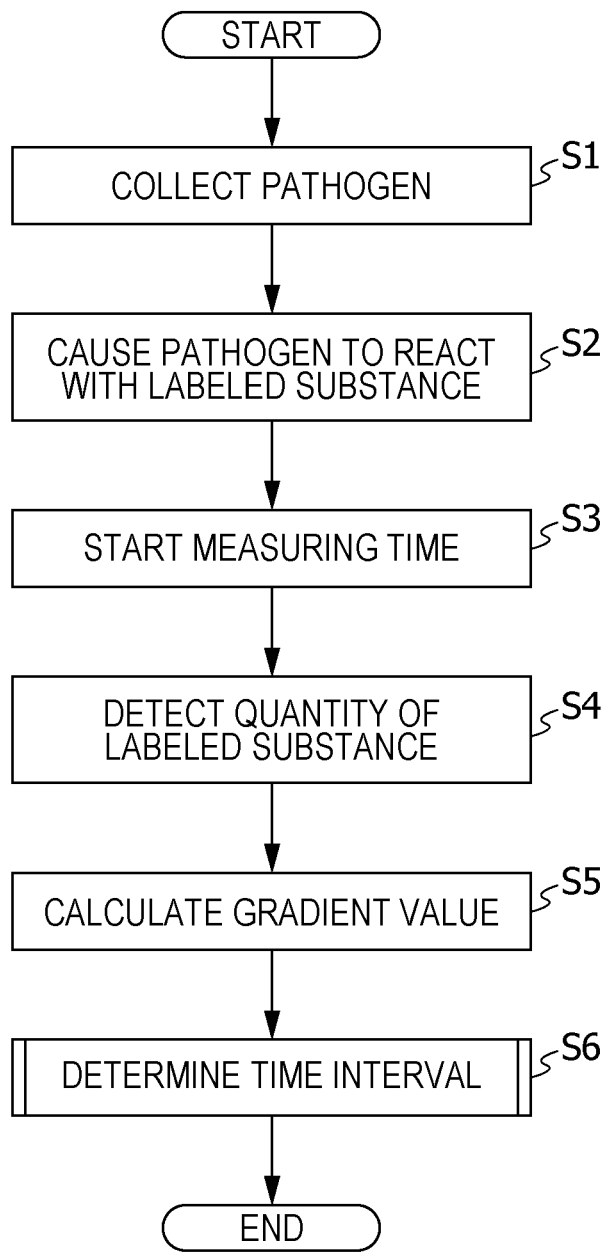
FIG. 11 is a flowchart illustrating an example of a pathogen detection method for the pathogen detection apparatus according to the embodiment.

FIG. 11 is a flowchart illustrating an example of the pathogen detection method for the pathogen detection apparatus 10 according to the present embodiment.

As illustrated in FIG. 11, in the pathogen detection apparatus 10, the collector 11 collects a pathogen in the air (S1).

The reactor 12 causes the pathogen collected by the collector 11 to react with a labeled substance (S2).

The time measurer 13 measures time from the start of reaction in the reactor 12 (S3).

The detector 14 detects the quantity of labeled substance, that is, the labeled substances 309 that have reacted with the pathogen (S4).

The controller 15 calculates a gradient value on the basis of a predetermined time period from the start of reaction measured by the time measurer 13 and the quantity of labeled substance detected by the detector 14 (S5).

Subsequently, the controller 15 determines, on the basis of the gradient value, a time interval to the next collection that is to be performed by the collector 11 (S6). The details of the process of determining the time interval in step S6 will be described below with reference to FIG. 12.

Figure 12:
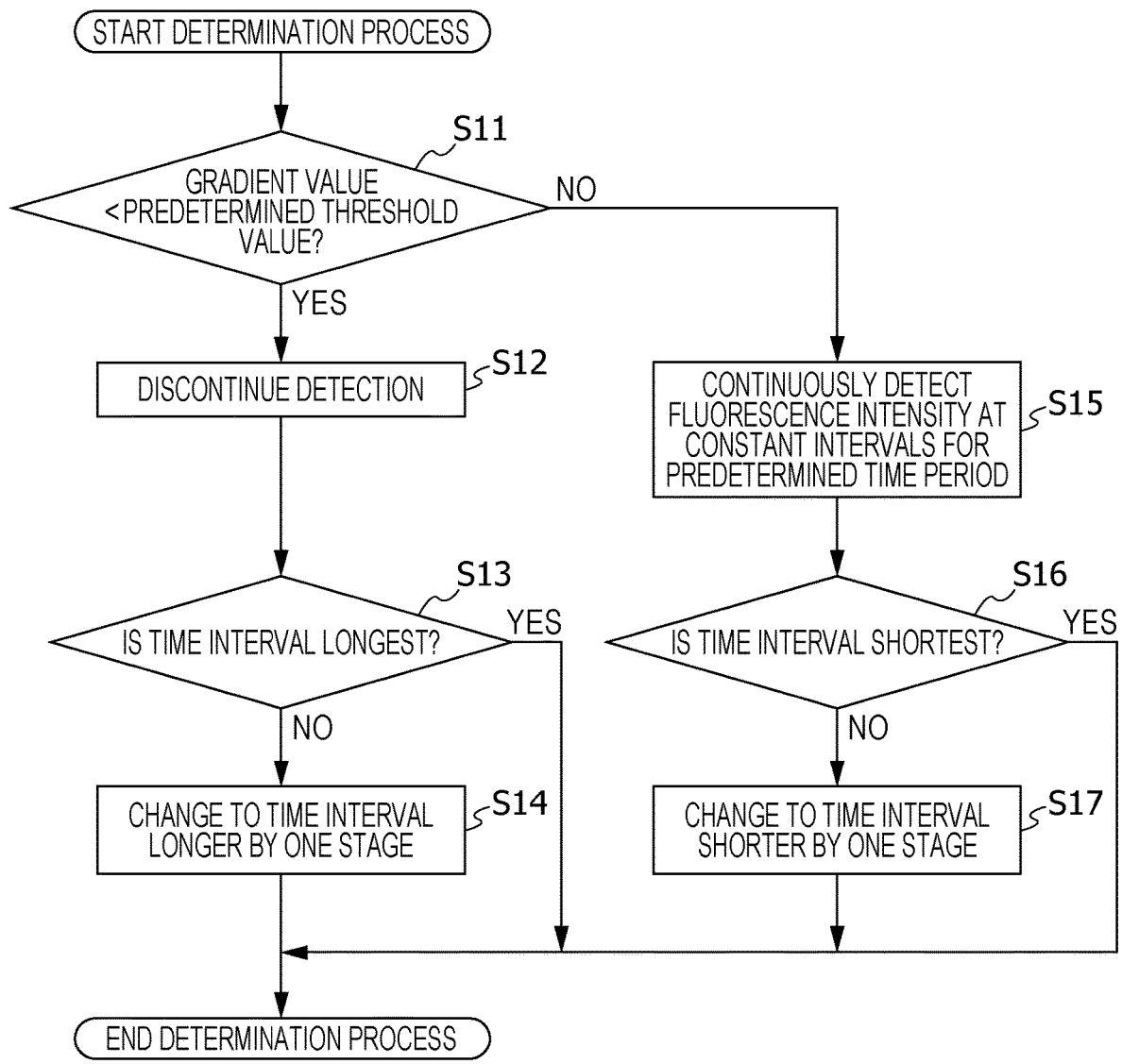
FIG. 12 is a flowchart illustrating an example of a process of determining a time interval.

FIG. 12 is a flowchart illustrating an example of the process of determining the time interval.

Upon start of the process of determining the time interval, the controller 15 determines whether or not the gradient value is smaller than the predetermined threshold value (S11).

In a case where the controller 15 determines that the gradient value is smaller than the predetermined threshold value (YES in S11), the controller 15 causes the detector 14 to discontinue detecting the quantity of labeled substance (S12). Accordingly, the detector 14 stops irradiation with laser light by the light source 208 and stops measurement of the fluorescence intensity by the detecting unit 214.

After that, the controller 15 determines whether or not the time interval to the next detection, that is, the next collection to be performed by the collector 11, is the longest time interval (S14). For example, the controller 15 holds time intervals in multiple stages and determines whether or not the currently set time interval is the longest time interval among the time intervals in the multiple stages. The time intervals in the multiple stages held by the controller 15 are three stages, for example, 30 minutes, 1 hour, and 2 hours. In this case, the controller 15 determines whether or not the currently set time interval is 2 hours.

In a case where the controller 15 determines that the time interval to the next collection to be performed by the collector 11 is not the longest time interval (NO in S13), the controller 15 changes the time interval to the time interval longer by one stage (S14). For example, if the current time interval is 30 minutes, the controller 15 changes the time interval to 1 hour. If the current time interval is 1 hour, the controller 15 changes the time interval to 2 hours.

On the other hand, in a case where the controller 15 determines that the time interval to the next collection to be performed by the collector 11 is the longest time interval (YES in S13), the controller 15 maintains the current time interval and ends the determination process.

Going back to step S11, in a case where the controller 15 determines that the gradient value is larger than or equal to the predetermined threshold value (NO in S11), the controller 15 causes the detector 14 to continuously detect the fluorescence intensity at constant intervals for a predetermined time period (S15). In other words, in this case, the controller 15 causes the detector 14 to continue detection. Here, the predetermined time period is, for example, 10 minutes.

After that, the controller 15 determines whether or not the time interval to the next detection, that is, the next collection to be performed by the collector 11, is the shortest time interval (S16). In other words, the controller 15 determines whether or not the currently set time interval is 30 minutes.

In a case where the controller 15 determines that the time interval to the next collection to be performed by the collector 11 is not the shortest time interval (NO in S16), the controller 15 changes the time interval to the time interval shorter by one stage (S17). For example, if the current time interval is 2 hours, the controller 15 changes the time interval to 1 hour. If the current time interval is 1 hour, the controller 15 changes the time interval to 30 minutes.

On the other hand, in a case where the controller 15 determines that the time interval to the next collection to be performed by the collector 11 is the shortest time interval (YES in S16), the controller 15 maintains the current time interval and ends the determination process.

Figure 13:
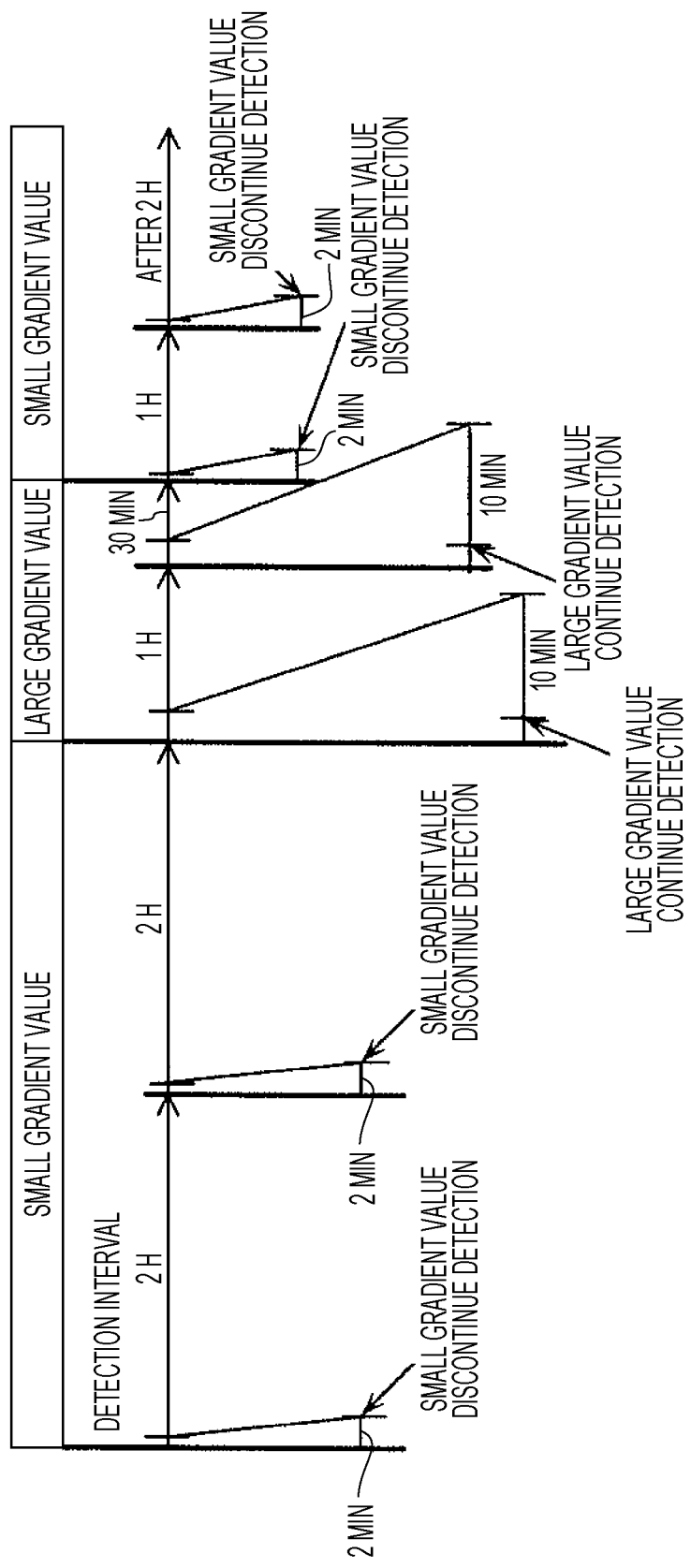
FIG. 13 is a diagram illustrating an example of switching in a detection operation.

As a result of performing the process of determining the time interval in this manner, the time interval for a detection operation can be switched as illustrated in FIG. 13.

FIG. 13 is a diagram illustrating an example of switching in the detection operation.

Here, the following situation is assumed: a state of "small gradient value" lasts for 4 hours in which the quantity of virus is small and the gradient value is smaller than the predetermined threshold value, then a state of "large gradient value" lasts for 1 hour and 30 minutes in which the quantity of virus is larger and the gradient value is larger than or equal to the predetermined threshold value, and then a state of "small gradient value" lasts in which the quantity of virus is small.

First, the controller 15 determines in step S11 that the gradient value is small in the first 2-minute measurement, and thus performs step S12 and causes the detector 14 to discontinue detection. If the controller 15 determines that the gradient value is small after a predetermined time period (for example, 20 seconds) elapses from the start of detection, the controller 15 may cause the detection to be discontinued at that time. In this case, it is assumed that the time interval to the next collection is set to the longest, that is, 2 hours. Thus, the controller 15 determines in step S13 that the time interval is set to the longest time interval, and ends the determination process while maintaining the current time interval.

Thus, the second detection is performed 2 hours after the start of the first detection. Also in the second detection, the controller 15 determines in step S11 that the gradient value is small and performs a process similar to that described above.

Thus, the third detection is performed 2 hours after the start of the second detection. In the third detection, the controller 15 determines in step S11 that the gradient value is large, and thus performs step S15 and continues detection by the detector 14 for a predetermined time period (for example, 10 minutes). Here, it is assumed that the reaction substantially reaches an equilibrium state in 10 minutes. In a case where more time is taken to reach the equilibrium state, the measurement may be continued for an extended time period. The controller 15 determines in step S16 that the time interval is not shortest, and changes the time interval to the time interval shorter by one stage, that is, from 2 hours to 1 hour.

Accordingly, the fourth detection is performed 1 hour after the start of the third detection. In the fourth detection, the controller 15 performs a process similar to the process in the third detection, and changes the time interval to the time interval shorter by one stage, that is, from 1 hour to 30 minutes.

Accordingly, the fifth detection is performed 30 minutes after the start of the fourth detection. In the fifth detection, the controller 15 determines in step S11 that the gradient value is small. Thus, the controller 15 performs step S12 and discontinues the detection by the detector 14. Subsequently, the controller 15 determines in step S13 that the time interval is not longest, and changes the time interval to the time interval longer by one stage, that is, from 30 minutes to 1 hour.

Accordingly, the sixth detection is performed 1 hour after the start of the fifth detection. In the sixth detection, the controller 15 performs a process similar to the process in the fifth detection, and changes the time interval to the time interval longer by one stage, that is, from 1 hour to 2 hours.

The longest time interval is 2 hours here, but the longest time interval may be 6 hours or half a day if no virus is detected for a long time. In addition, the shortest time interval is not limited to 30 minutes, and may be set to a time interval that is necessary for one detection in accordance with the detection ability of the pathogen detection apparatus 10.

Advantages and the Like

In the pathogen detection apparatus 10 according to the above-described embodiment, the time interval to the next collection that is to be performed by the collector 11 is determined in accordance with the gradient value, and thus the time period from when a detection is finished to when the next detection is performed is appropriately determined. Thus, a pathogen detection frequency is decreased, and thereby waste of consumables or energy can be reduced.

In the pathogen detection apparatus 10, the detector 14 includes the light irradiator 14a that irradiates the reactor 12 with excitation light, and detects the quantity of labeled substance on the basis of fluorescence generated by the labeled substances 309 as a result of irradiation with the excitation light. In this way, the quantity of labeled substance is detected by detecting fluorescence, and thus the quantity of labeled substance can be effectively detected.

In the pathogen detection apparatus 10, the detector 14 detects an intensity of the fluorescence generated by the labeled substances 309 as a result of irradiation with the excitation light, and detects the quantity of labeled substance on the basis of the detected intensity of the fluorescence and chronological changes in attenuation of the intensity of the fluorescence detected by irradiating the labeled substance with the excitation light, the chronological changes being stored in advance. In this way, the quantity of labeled substance is detected on the basis of the intensity of the fluorescence and the chronological changes in attenuation of the fluorescence, and thus the gradient value can be calculated in an early stage after the start of reaction.

In the pathogen detection apparatus 10, the light irradiator 14a emits the excitation light at predetermined intervals. The detector 14 detects chronological changes in the quantity of labeled substance. The controller 15 calculates the gradient value by dividing, by the predetermined time period, a result obtained by subtracting a first quantity of labeled substance from a second quantity of labeled substance in the chronological changes, the first quantity of labeled substance being detected through irradiation with the excitation light at a first timing that is the start of reaction, the second quantity of labeled substance being detected through irradiation with the excitation light at a second timing that is the predetermined time period after the first timing. Thus, the second quantity of labeled substance can be appropriately detected, and the gradient value in an early stage after the start of reaction can be accurately calculated.

In the pathogen detection apparatus 10, the controller 15 changes the time interval to a longer time interval in a case where the gradient value is smaller than a predetermined threshold value. Specifically, in a case where the gradient value is smaller than the predetermined threshold value, the controller 15 determines that the quantity of pathogen is small, and changes the time interval to the next pathogen detection to a longer time interval. Thus, a pathogen detection frequency can be decreased in a case where the quantity of pathogen is small.

In the pathogen detection apparatus 10, the controller 15 changes the time interval to a shorter time interval in a case where the gradient value is larger than or equal to the predetermined threshold value. Specifically, in a case where the gradient value is larger than or equal to the predetermined threshold value, the controller 15 determines that the quantity of pathogen is large, and changes the time interval to the next pathogen detection to a shorter time interval. Thus, a pathogen detection frequency can be increased in a case where the quantity of pathogen is large, and a situation can be prevented from occurring where detection is not performed for a long time despite the presence of a pathogen.

In the pathogen detection apparatus 10, the controller 15 causes the detector 14 to continue detecting the quantity of labeled substance in a case where the gradient value is larger than or equal to the predetermined threshold value, and causes the detector 14 to discontinue detecting the quantity of labeled substance in a case where the gradient value is smaller than the predetermined threshold value. That is, in a case where the gradient value is larger than or equal to the predetermined threshold value, the controller 15 determines that the quantity of pathogen is large, and is capable of estimating the quantity of pathogen by using a result obtained by continuing the detection of the quantity of labeled substance. In a case where the gradient value is smaller than the predetermined threshold value, the controller 15 determines that the quantity of pathogen is small and that it is not necessary to estimate the quantity of pathogen, and is capable of discontinuing the detection of the quantity of labeled substance. As a result of the discontinuation, the energy consumption of the pathogen detection apparatus can be reduced.

In the above-described embodiment, the individual components may be constituted by dedicated hardware or may be implemented by executing a software program suitable for the individual components. The individual components may be implemented when a program executing unit of a CPU or processor reads out and executes the software program recorded on a recording medium, such as a hard disk or a semiconductor memory. Here, the software that implements the pathogen detection method according to the above-described embodiment is the following program.

The program causes a computer to execute a pathogen detection method including: collecting a pathogen in air; causing the collected pathogen to react with a labeled substance; measuring time from start of reaction; detecting a quantity of labeled substance that has reacted with the pathogen; and calculating a gradient value on the basis of a measured predetermined time period from the start of reaction and the detected quantity of labeled substance, and determining, on the basis of the gradient value, a time interval to next collection that is to be performed.

The pathogen detection apparatus and the pathogen detection method according to an aspect or aspects of the present disclosure have been described on the basis of the embodiment. The present disclosure is not limited to the embodiment. An embodiment established by applying a modification conceived by a person skilled in the art to the above embodiment, and an embodiment established by combining components in different embodiments may be included in the scope of an aspect or aspects of the present disclosure without deviating from the gist of the present disclosure.

The present disclosure is useful as a pathogen detection apparatus and a pathogen detection method that are capable of reducing detection frequency to reduce waste of consumables or energy.

What is claimed is:

1. A pathogen detection apparatus comprising:
- a collector that collects a pathogen in air;
- a reactor that causes the pathogen collected by the collector to react with a labeled substance;
- a time measurer that measures time from start of reaction in the reactor;
- a detector that detects a quantity of labeled substance that has reacted with the pathogen; and
- a controller, wherein
- the controller calculates a gradient value on the basis of a predetermined time period from the start of reaction measured by the time measurer and the quantity of labeled substance detected by the detector, and determines, on the basis of the gradient value, a time interval to next collection that is to be performed by the collector.

2. The pathogen detection apparatus according to claim 1, wherein the detector includes a light irradiator that irradiates the reactor with excitation light, and detects the quantity of labeled substance on the basis of fluorescence generated by the labeled substance as a result of irradiation with the excitation light.

3. The pathogen detection apparatus according to claim 2, wherein the detector detects an intensity of the fluorescence generated by the labeled substance as a result of irradiation with the excitation light, and detects the quantity of labeled substance on the basis of the detected intensity of the fluorescence and chronological changes in attenuation of the intensity of the fluorescence detected by irradiating the labeled substance with the excitation light, the chronological changes being stored in advance.

4. The pathogen detection apparatus according to claim 2, wherein
- the light irradiator emits the excitation light at predetermined intervals,
- the detector detects chronological changes in the quantity of labeled substance, and
- the controller calculates the gradient value by dividing, by the predetermined time period, a result obtained by subtracting a first quantity of labeled substance from a second quantity of labeled substance in the chronological changes, the first quantity of labeled substance being detected through irradiation with the excitation light at a first timing that is the start of reaction, the second quantity of labeled substance being detected through irradiation with the excitation light at a second timing that is the predetermined time period after the first timing.

5. The pathogen detection apparatus according to claim 1, wherein
- the collector collects a first pathogen at a first time, the first pathogen being the pathogen,
- the collector collects a second pathogen at a second time, collects a third pathogen at a third time, and does not collect a pathogen between the second time and the third time except for the first time, the second time being before the first time, the third time being after the first time,
- the time interval is an interval between the first time and the third time, and
- in a case where the gradient value related to the first pathogen is smaller than a predetermined threshold value, the controller sets the time interval to be longer than an interval between the second time and the first time.

6. The pathogen detection apparatus according to claim 1, wherein
- the collector collects a first pathogen at a first time, the first pathogen being the pathogen,
- the collector collects a second pathogen at a second time, collects a third pathogen at a third time, and does not collect a pathogen between the second time and the third time except for the first time, the second time being before the first time, the third time being after the first time,
- the time interval is an interval between the first time and the third time, and
- in a case where the gradient value related to the first pathogen is larger than or equal to a predetermined threshold value, the controller sets the time interval to be shorter than an interval between the second time and the first time.

7. The pathogen detection apparatus according to claim 1, wherein the controller causes the detector to continue detecting the quantity of labeled substance in a case where the gradient value is larger than or equal to a predetermined threshold value, and causes the detector to discontinue detecting the quantity of labeled substance in a case where the gradient value is smaller than the predetermined threshold value.

8. A pathogen detection method comprising:
- collecting a pathogen in air;
- causing the collected pathogen to react with a labeled substance;
- measuring time from start of reaction;
- detecting a quantity of labeled substance that has reacted with the pathogen; and
- calculating a gradient value on the basis of a measured predetermined time period from the start of reaction and the detected quantity of labeled substance, and determining, on the basis of the gradient value, a time interval to next collection that is to be performed.

* * * * *